(12) United States Patent
Azocar

(10) Patent No.: US 8,372,048 B1
(45) Date of Patent: Feb. 12, 2013

(54) METHOD AND DEVICE FOR TISSUE OXYGENATION

(76) Inventor: Jose Azocar, Hartford, CT (US)

( * ) Notice: Subject to any disclaimer, the term of this patent is extended or adjusted under 35 U.S.C. 154(b) by 675 days.

(21) Appl. No.: 12/574,727

(22) Filed: Oct. 7, 2009

Related U.S. Application Data

(63) Continuation-in-part of application No. 11/405,970, filed on Apr. 17, 2006, now abandoned.

(60) Provisional application No. 60/672,913, filed on Apr. 18, 2005.

(51) Int. Cl.
*A61M 1/00* (2006.01)

(52) U.S. Cl. .................. 604/304; 604/289; 602/41

(58) Field of Classification Search ............ 602/41; 606/202; 424/443; 604/289, 290, 304, 305, 604/307
See application file for complete search history.

(56) References Cited

U.S. PATENT DOCUMENTS

| | | | |
|---|---|---|---|
| 4,113,652 A | 9/1978 | Yoshikawa et al. |
| 4,287,995 A | 9/1981 | Moriya |
| 4,365,831 A | 12/1982 | Bourne |
| 4,510,162 A | 4/1985 | Nezat |
| 4,536,409 A | 8/1985 | Farrell |
| 4,702,966 A | 10/1987 | Farrell et al. |
| 4,752,091 A | 6/1988 | Jackson |
| 5,310,497 A | 5/1994 | Ve Speer et al. |
| 5,399,289 A | 3/1995 | Speer et al. |
| 6,343,948 B1 | 2/2002 | Nutzel |
| 6,479,160 B1 | 11/2002 | Tsai et al. |
| 6,607,795 B1 | 8/2003 | Yang et al. |
| 6,709,724 B1 | 3/2004 | Teumac et al. |
| 6,772,807 B1 | 8/2004 | Tang |
| 6,821,594 B2 | 11/2004 | Wantanabe et al. |
| 6,846,025 B2 | 1/2005 | Sclater et al. |

OTHER PUBLICATIONS

Fear et al. "The Effect of Dressings on the Production of Exudate from Venous Leg Ulcers", Wounds, 1996; 8:145-50.

*Primary Examiner* — Melanie Hand
(74) *Attorney, Agent, or Firm* — Doherty Wallace Pillsbury & Murphy, P.C.

(57) ABSTRACT

A tissue oxygenation device for creating and oxygen gradient that promotes the diffusion of oxygen from underlying capillaries and subcutaneous tissue up through and over an overlying target site of skin tissue, comprising: a gas impermeable encasement which forms a chamber which surrounds the target site when the encasement is positioned over the target site; an oxygen scavenging member comprising an oxygen scavenger, wherein the oxygen scavenging member is contained within the chamber such that the oxygen scavenger is exposed to oxygen within the chamber, and further wherein the oxygen scavenger removes oxygen contained within the chamber at a continuous rate; and an adjustable cuff, wherein the adjustable cuff comprises a pliable body which is attached to the gas impermeable encasement on an end of the body and to the target site at another end of the body; wherein the gas impermeable encasement and the adjustable cuff jointly operate to seal the target site within the chamber.

7 Claims, 7 Drawing Sheets

A-A

METHOD AND DEVICE FOR TISSUE OXYGENATION

CROSS-REFERENCE TO RELATED APPLICATIONS

This application is a continuation-in-part application of U.S. patent application Ser. No. 11/405,970 filed on Apr. 17, 2006 (now pending), which claims the benefit of U.S. Provisional Application No. 60/672,913 filed on Apr. 18, 2005 (now expired).

BACKGROUND OF THE INVENTION

1. Field of the Invention

The present invention relates to medical devices and processes for the promotion of the healing of skin tissue by increasing tissue oxygenation through and over the skin tissue under non-hyperbaric conditions.

2. Background of the Invention.

The integrity of local skin microcirculation and appropriate levels of skin oxygenation are critical factors in the maintenance of tissue integrity and in the promotion of wound healing. A common method used to increase skin tissue oxygenation involves hyperbaric oxygen therapy ("HBOT"). However, although HBOT may be efficient in some instances in increasing tissue oxygenation, it remains a cumbersome treatment option, and its use is limited to no more than a few hours per week. Additionally, some commonly observed side effects resulting from use of HBOT include e.g., ear and sinus trauma, oxygen toxicity to the central nervous system and to pulmonary tissue, and acceleration of cataract maturation.

Accordingly, what is needed is a device that can treat oxygen deprived tissue in an efficient and cost-effective manner, and which reduces the risk of the occurrence of certain side effects associated with the use of HBOT-based treatment methods.

SUMMARY OF INVENTION

The tissue oxygenation device ("TOD") of the present invention is designed to overcome or alleviate some of the problems associated with the use of HBOT in the oxygenation of damaged skin tissue. For example, the TOD is designed to increase oxygenation only at the desired target site, and allows for user mobility and for the use of the TOD for longer periods of time as compared to HBOT.

When properly applied and used, the TOD promotes the formation of an oxygen gradient to increase the flow of oxygen through and over a desired area of skin tissue via the diffusion of oxygen from the subcutaneous tissue and capillary bed, which closely underlie target site skin tissue. The TOD is shaped to fit the contours of a target site, i.e., the area of skin tissue through and over which an increase in oxygenation is desired, such as, for example, where there is a skin lesion or other wound site, and to enclose such target site within a chamber under seal so as to isolate the target site from the ambient air.

Accordingly, the chamber of the TOD is designed to enclose the target site in a substantially air tight manner such that, when the TOD is properly applied and used, appreciable amounts of oxygen cannot escape from outside the chamber and into the ambient air, and such that appreciable amounts of oxygen cannot enter into the chamber from the ambient air. The TOD further comprises an oxygen scavenger which is selected to continuously and steadily remove oxygen from within the chamber. This steady and continuous removal of oxygen from the chamber via the oxygen scavenger, along with the substantially air tight seal created around the chamber, creates an oxygen concentration gradient which promotes the natural diffusion of oxygen from the capillary bed and subcutaneous tissue closely surrounding the target site, and through, out, and over the overlying skin tissue.

In an exemplary embodiment, in addition to the oxygen scavenger, the TOD comprises an outermost gas impermeable encasement which provides a substantially air-tight barrier between the target site and the ambient air, i.e., the air surrounding an exterior side wall of the encasement. Additionally, the TOD may further comprise a cuff which assists in attaching the TOD to the target site, and which also assists in sealing the target site within the chamber. In an exemplary embodiment, the cuff allows the TOD to be securely fitted and sealed to a variety of sized and shaped users; accordingly, a circumference of the seal is variable.

In another exemplary embodiment, the oxygen scavenger is integrated into a composite, wherein, in addition to the oxygen scavenger, the composite comprises at least one or more of a barrier layer, a moisture/exudate absorbing layer, and an adhesive. Via the adhesive, the composite may be applied to an interior wall of the gas impermeable encasement, i.e., the wall which is directed towards the target site. The composite is preferably flexible such that it can rest and fit against the contours and shape of the encasement.

Again, as would be appreciated upon a reading of the present disclosure, following basic laws of diffusion, as a result of (1) the steady and continuous removal of oxygen from the chamber via the oxygen scavenger, and (2) the substantially air-tight seal formed around the target site by the encasement and the cuff, a continuous outward supply of oxygen flows from the underlying blood capillaries and subcutaneous tissue, and eventually out through and over the skin tissue of the target site enclosed within the chamber.

Where the more expeditious establishment of the oxygen gradient and outward diffusion of oxygen is desired, oxygen within the chamber may be initially removed or purged by configuring the TOD to allow for the controlled flow of at least one of oxygen, nitrogen, and any other oxygen removing gas which does not affect the effectiveness of the TOD, in and out of the chamber.

To assist in detecting and monitoring the oxygen levels inside the chamber when the TOD is properly positioned over the target site and used, one or more oxygen chamber sensors may be fitted onto the TOD and placed in communication with a data processing and viewing system, such as a computer and monitor. To detect and monitor skin tissue oxygenation, and/or skin tissue temperature, one or more skin tissue oxygenation sensors and/or skin temperature sensors, may be fitted onto the TOD and placed in communication with the data processing and viewing system.

DETAILED DESCRIPTION OF THE INVENTION

Figure 1:
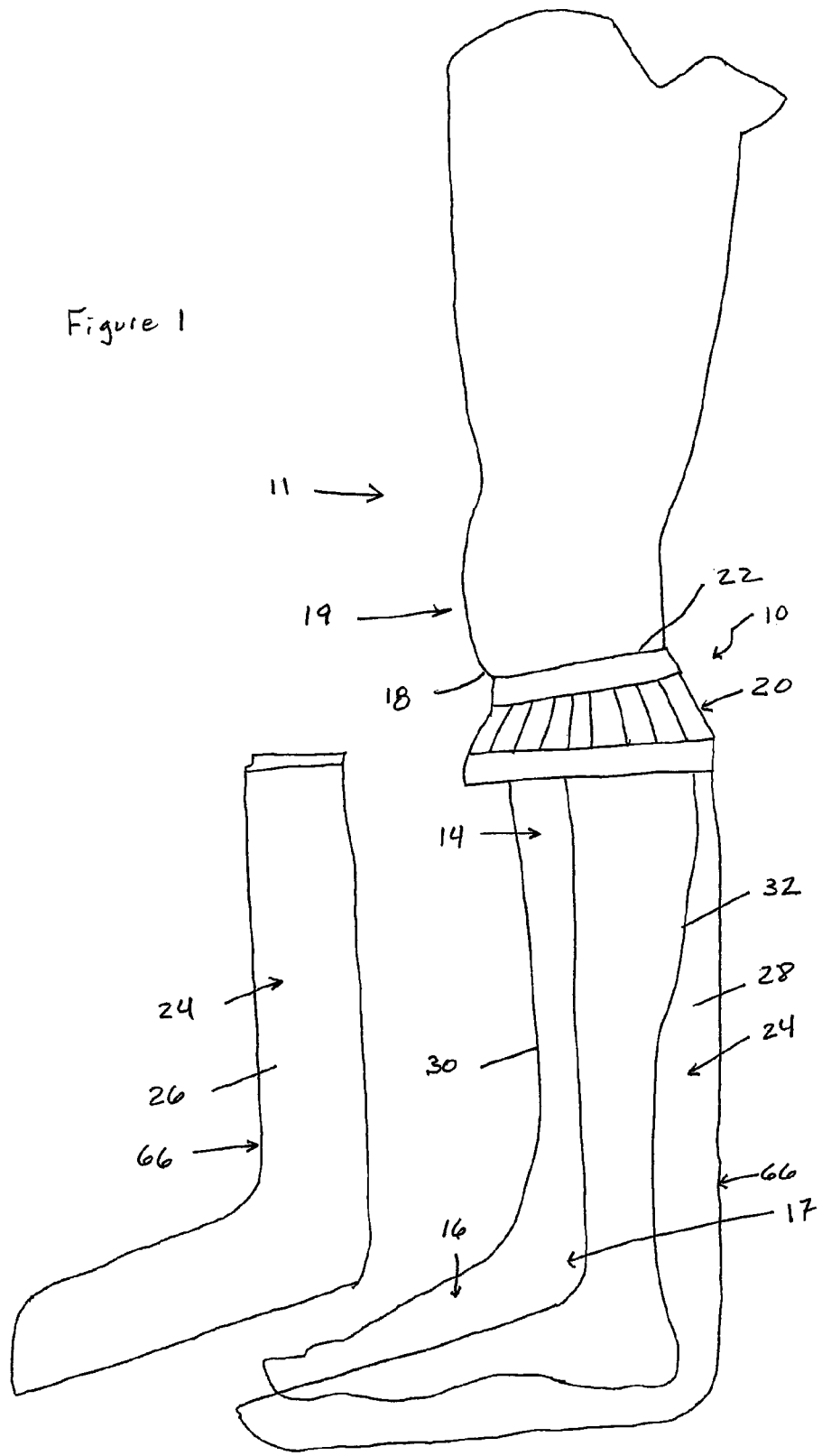
FIG. 1 is a schematic depicting an exemplary embodiment of a TOD.

Supplying oxygen to skin tissue in need of increased oxygen for therapeutic purposes, such as in the case of skin lesions, such as is oftentimes seen in peripheral vascular diseases, and other situations where the circulation and/or the source of oxygen is compromised, is essential to skin tissue healing. The TOD of the present invention increases the amount of oxygen over a target site of skin tissue by taking advantage of Fick's First Law of Diffusion ("Fick's Law"), along with the fact that skin tissue is oxygen permeable.

Fick's Law describes the passive movement of molecules down a concentration gradient. The following equation, based upon Fick's Law, gives the steady state relationship for the rate of oxygen transfer ("mass transfer"):

$$W = \frac{(C_1 - C_2)(A)(D)}{L}$$

Where:
W=mass transfer rate;
$C_1$=higher concentration of oxygen in the capillaries;
$C_2$=lower concentration of oxygen above the tissue;
A=tissue area across which diffusion occurs;
D=diffusion or permeability coefficient; and
L=thickness of the damaged tissue (a.k.a. length of the diffusion path).

Using this formula, the flux of oxygen and the direction of its diffusion can be calculated. Since, under normal conditions, the concentration of oxygen is greater over the skin then under the skin, the oxygen flux usually transverses a path from outside to inside the skin. Therefore, pursuant to Fick's Law, the ability of oxygen to diffuse from the capillaries and subcutaneous tissue, through the skin tissue, and eventually out of the body, can occur if the concentration of oxygen outside the body is lower than the concentration of oxygen inside the body.

The TOD of the present invention, when properly applied and used, causes a constant outward diffusion of oxygen from nearby underlying blood capillaries and subcutaneous tissue, to a target skin tissue (the "target site"), and eventually out through and over the target site. Utilizing the principles of Fick's Law, again which postulates that oxygen flows from regions of high concentration to regions of low concentration in a magnitude that is proportional to the oxygen concentration gradient, the TOD of the present invention is designed to seal the target site within a chamber so that an appreciable amount of ambient air, i.e., the air outside the chamber and off from which the target site is substantially closed, does not enter the chamber of the TOD which encloses the target site.

The chamber of the TOD is formed, at least in part, by a gas impermeable encasement. The primary purpose of the gas impermeable encasement is twofold: to prevent an appreciable amount of ambient air from entering the chamber, and to prevent an appreciable amount of oxygen from exiting the chamber and flowing into the ambient air. Preferably, the gas impermeable encasement is ergonomically shaped to fit the contours of a variety of shaped and sized users. An exemplary outermost gas impermeable encasement comprises a thermoplastic polymer resin, such as a medical-grade polyvinylchloride (PVC) or polypropylene.

In addition to the gas impermeable encasement, the TOD further comprises an oxygen scavenging member comprising an oxygen scavenger. Preferably at a continuous and steady rate, the oxygen scavenger removes the oxygen contained within the chamber which encloses the target area, thereby reducing the oxygen concentration within the chamber. This depletion of oxygen in the substantially air tight chamber naturally causes an oxygen gradient and, hence, an increased flow of oxygen from the nearby subcutaneous tissue and capillaries, up, through and over the target site; and into the chamber.

The oxygen scavenger can be any currently known or unknown material capable of effectively removing oxygen from the chamber, which is compatible with the other component(s) of the device, and which is acceptable for use on or near the target site. For example, the oxygen scavenger may comprise one or more of oxygen scavenging powders, pellets, and the like formed from materials such as, e.g., iron and iron compounds, such as, iron sulfate.

In addition to the oxygen scavenger, the oxygen scavenging member may further comprise a thermoplastic film. An exemplary oxygen scavenging member is described in U.S. Pat. No. 5,089,323 to Nakae et al., which discloses an oxygen-absorbing sheet comprising a thermoplastic resin and an oxygen absorbent made of iron powder. Another exemplary oxygen scavenging member is described in U.S. Pat. No. 6,063,503 to Hatakeyama et al., which teaches an oxygen-absorbing multi-layer film comprising a deoxidizing resin layer containing iron powder. Another exemplary oxygen scavenger is described in U.S. Pat. No. 6,391,407 to Kashiba et al., which discloses an oxygen-absorbing layer containing an iron deoxidizing agent.

U.S. Pat. No. 6,503,587 to Kashiba et al. ("'587") discloses an oxygen-absorbing multi-layer film suitable for preserving food. Referring to FIG. 1 of '581, the multi-layer film comprises an outer layer 1 to which pigment is added; a contiguous thermoplastic resin layer 3; a gas barrier layer 4; and a protecting layer 5. Layers 3, 4, 5 are successively laminated on layer 1. Particles of an oxygen-absorbing agent 2 (preferably, iron powder) are locally interspersed between layers 1 and 3, with some of the particles being distributed in the interface between the adjacent layers (1 and 3) while some particles are present in one of the layers (1 or 3) and the other particles are present in both the layers (1 and 3). The disclosure of '587 is hereby incorporated in its entirety by reference.

The oxygen scavenging member may also comprise one or more types of desiccants to reduce the humidity of the chamber. Although the desiccant may be selected from a wide variety of desiccants, a preferable desiccant comprises at least one of a silica gel, Desi Paste™, which is provided by Sud Chemie, and the like.

The TOD further comprises a gas impermeable, flexible cuff which assists in engaging and disengaging the TOD to and from the target site. The cuff also serves to create a substantially air tight seal that isolates the target site and the chamber from appreciable amounts of the ambient air, and which also restricts the flow of an appreciable amount of oxygen from the chamber and out into the ambient air. Additionally, in an exemplary embodiment, the cuff may also be used to adjust the TOD to the individual size requirements of a particular user; in this manner, and as will be further appreciated below, a circumference of the cuff may be variable.

The cuff, which may be formed from a non-synthetic or a synthetic flexible rubber material, may be attached to the gas impermeable encasement via, for example, an adhesive. The adhesive may further be used to attach the cuff to the target site. The adhesive may be formed from a wide variety of presently known materials or from future known materials, all of which properly fixedly attach to the target site when necessary, but which are also relatively removable from the target site when necessary, and which are considered relatively safe for application to the target site. Nevertheless, exemplary adhesive materials include without limitation, one or more of a classical pressure sensitive adhesive, a hydrocolloid PSA, a hydrogel, and the like.

In an exemplary embodiment, the TOD may also comprise at least one or more of the following: a barrier layer, a moisture/exudate absorbing layer, and an adhesive layer. The barrier layer serves to buffer the target site from the oxygen scavenging member.

The barrier layer may comprise a wide range of materials so long as the barrier layer is oxygen permeable and considered relatively safe for application to or near the target site. Additionally, in a preferred embodiment, the barrier layer is also non-absorbent. In an exemplary embodiment, the barrier layer comprises at least one of tegaderm hydrocolloid (3M), Mepitel (Molnlycke Health Care Inc) Melitex Lite Bioflex 130, Bioflex 235 (Scapa North America), and the like, wherein tegadeiin hydrocolloid is especially preferred.

The moisture/exudate absorbing layer absorbs skin moisture and exudates, and in an exemplary embodiment comprises at least one of aquacel hydrofiber hydrocolloid, Mepore (Molnlycke Health Care Inc), Tegaderm THIN hydrocolloid dressing (3M), Melolite (Smith and Nephew Inc), and the like, wherein an aquacel hydrofiber hydrocolloid is especially preferred. One or more moisture/exudate absorbing layers may be used according to the volume of exudates expected to be absorbed.

The adhesive layer may be used to attach the oxygen scavenging member, and, when used, the barrier layer(s) and/or the moisture/exudate absorbing layer(s) to the gas impermeable encasement. Accordingly, the adhesive layer may be selected from a wide variety of materials so long as the materials allow the adhesive layer to be securely attached to the encasement during application of the TOD to a user, ensures that the adhesive does not affect the efficacy of the TOD, and is regarded as appropriate for use on the target site.

In an exemplary embodiment, the oxygen scavenging member and at least one or more of the barrier layer, and the moisture/exudate layer, and the adhesive layer, is formed as a multi-layered composite, and more preferably, as a multi-layered laminated composite. An exemplary lamination process may occur via the process disclosed in '587 and in U.S. Pat. No. 6,746,772 to Kashiba et al. Preferably, the composite is pliable and flexible such that the composite may be disposed on and fitted to the contours and shape of the interior side of the gas impermeable encasement.

The TOD may further comprise a means whereby the oxygen concentrations in the chamber may be more quickly decreased to hasten the diffusion of oxygen molecules from the nearby capillaries and subcutaneous tissue to the overlying nearby target. In an exemplary embodiment, such oxygen purging means may comprise a porthole formed through the gas impermeable encasement and a bivalve disposed within such porthole such that the bivalve extends out from an exterior side of the gas impermeable encasement, and extends into the chamber from the interior side of the gas impermeable encasement. The bivalve may comprise any conventionally known bivalve, and which is suitable for use with the TOD.

Nitrogen gas or any other oxygen binding gas, e.g., may be added into the chamber via the bivalve, and the bound oxygen or free oxygen may be released from the chamber via the bivalve.

The TOD may be designed to allow for the detection and monitoring of oxygen concentrations within the chamber, and/or the oxygenation at one or more points on the target site. To that end, the gas impermeable encasement may include one or more portholes each of which may hold an oxygen chamber sensor, as known in the art, and which measures the oxygen concentration in the chamber. Additionally or alternatively, the gas impermeable encasement may include one or more portholes, each of which may hold a tissue oxygenation sensor, as known in the art, and which measures the oxygenation of the skin tissue in the area surrounding the tissue oxygenation sensor. Each sensor may be in communication with a data receiver and data detection device, such as a computer processor and a monitor, as is known, or will be known, in the art.

An exemplary method for applying the TOD to a target site comprises selecting a target site, wherein exemplary target sites include without limitation, an appendage (e.g., a hand, an arm, a foot, or a leg), a torso, and the like. The exemplary method may further comprise providing the gas impermeable encasement, one or more composites, and the cuff. In an exemplary embodiment, the gas impermeable encasement is divided into an anterior portion which is to be disposed over an anterior portion of the target site, and a posterior portion, which is to be disposed over a posterior portion of the target site. The one or more composites are strategically applied to those portions of the posterior and/or the anterior portions of the encasement in order to achieve the oxygen gradient and the desired rates of oxygen diffusion from the nearby subcutaneous tissue and capillaries, and through and over the target site contained within the chamber. The composite is fixed to the interior side of the gas impermeable encasement by disposing the adhesive layer of the composite directly onto the interior side. Additionally, because the composite is formed to be flexible and pliable, when attached to the encasement, the composite fits the shape and contours of the encasement.

Once the composite has been placed on its respective anterior and/or posterior portion of the encasement, the anterior and posterior portions of the gas impermeable encasement may be placed over the respective target site. The anterior and posterior portions are attached to each other to form a substantially air tight seal between the two portions of the gas impermeable encasement. In a preferred embodiment, the anterior and posterior portions are sealed to create a closed distal end and an open-ended proximal end. The cuff may then be applied to the open-ended proximal end of the gas impermeable encasement to seal the target site within the chamber.

The anterior and posterior portions may be configured to form a seal pursuant to the teachings of U.S. Pat. No. 6,772,807 to Tang ("'807"), wherein such teachings are included herein by reference in their entirety. More specifically, anterior portion may be configured such as is taught by reference number 13 in '807, and posterior portion may be configured such as is taught by reference number 22 in '807, or vice versa.

Additionally, each of anterior and posterior portions may comprise complementary latching mechanisms which further assist in creating a substantially air-tight seal between the anterior and posterior portions. Exemplary latching mechanisms may include, without limitation, those such as are taught in U.S. Pat. Nos. 4,365,831; 6,343,948; 4,752,091; and 6,846,025; all of which are incorporated by reference herein in their entirety.

Exemplary embodiments of the TOD and its method of use shall now be discussed with reference to the figures, wherein it is to be understood that the figures are in no way limiting, but are provided for illustrative purposes only. As such, the invention is not to be limited to such depicted embodiments, but shall be covered under any and all variations and modifications to the depicted embodiments as would occur to one of ordinary skill in the art based upon a reading of the present disclosure.

Figure 3:
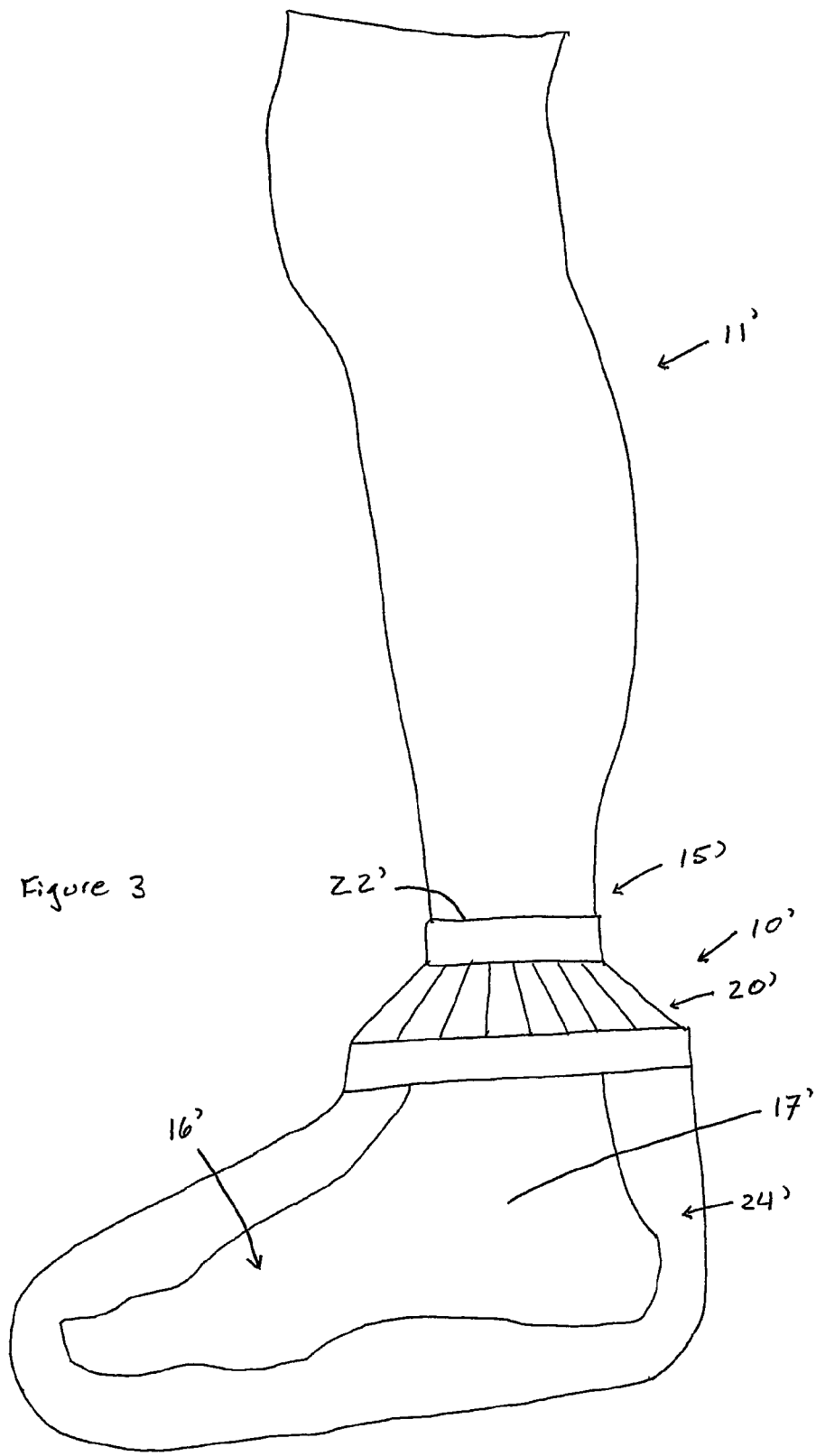
FIG. 3 is a schematic depicting another exemplary embodiment of the TOD.

Referring to FIGS. 1 and 3, exemplary TOD 10 and TOD 10' respectively depict placement of the TOD around various appendages. More specifically, FIG. 1 depicts the placement of TOD 10 onto and around an appendage 11 comprising a lower leg 14, a foot 16, and an ankle 17 such that a top edge 22 of a cuff 20 of TOD 10 terminates at a bottom 18 of a knee 19. FIG. 3, depicts placement of TOD 10' onto and around an appendage 11' comprising a foot 16' and an ankle 17' such that a top edge 22' of a cuff 20' terminates just above ankle 17' and below a lower calf 15'. Other than the obvious differences and variations in the size and shape of TOD 10 and 10', TOD 10 and TOD 10' are identical in terms of their materials, structure, and functions. Accordingly, the remainder of the specification will be structured around a description of TOD 10, wherein it is to be understood that such description applies equally to a description of TOD 10'. It is additionally noted that TOD 10 may also be accommodated and modified in obvious ways to fit other appendages and/or body parts not depicted in the figures, including for example, all or a portion of an arm, leg, chest, neck, torso, and the like.

Figure 2:
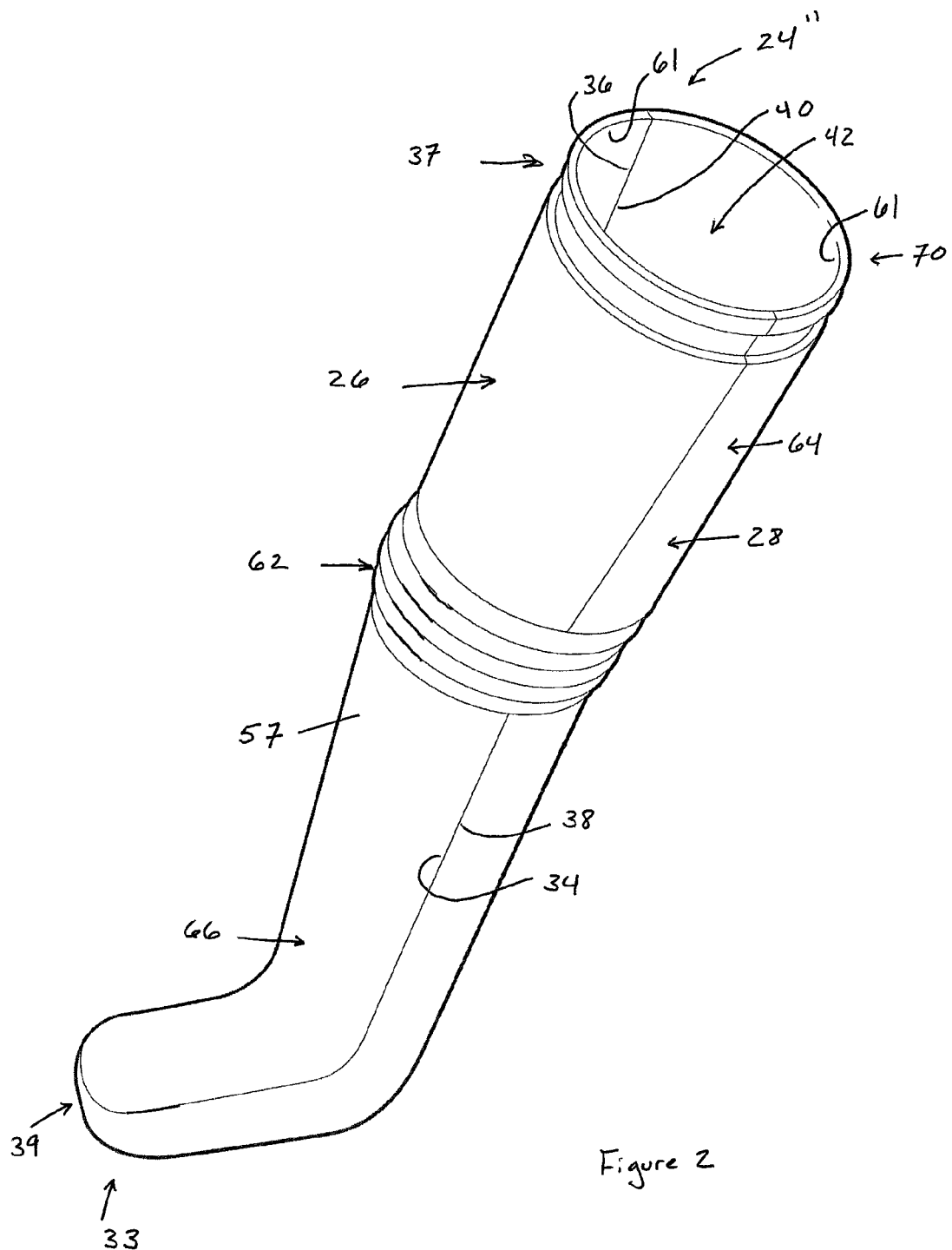
FIG. 2 is a schematic depicting an exemplary gas impermeable encasement.

FIG. 2 depicts a gas impermeable encasement 24" which is configured to fit around an appendage 11" comprising an upper leg 23, knee 19, lower leg 14, foot 16, and ankle 17. In addition to a lower member 66, which surrounds lower leg 14, foot 16, and ankle 17, gas impermeable encasement further comprises a knee adaptor 62 and an upper leg member 64, wherein knee adaptor 62 is specially configured to wrap around the knee of the target site, and upper leg member 64 is configured to wrap around the upper leg of the target site. It is noted that gas impermeable encasement 24" may be used as a component of forming a TOD having essentially the same properties and characteristics as TOD 10 and 10', where the only difference relates to size and geometrical configurations.

Figure 7:
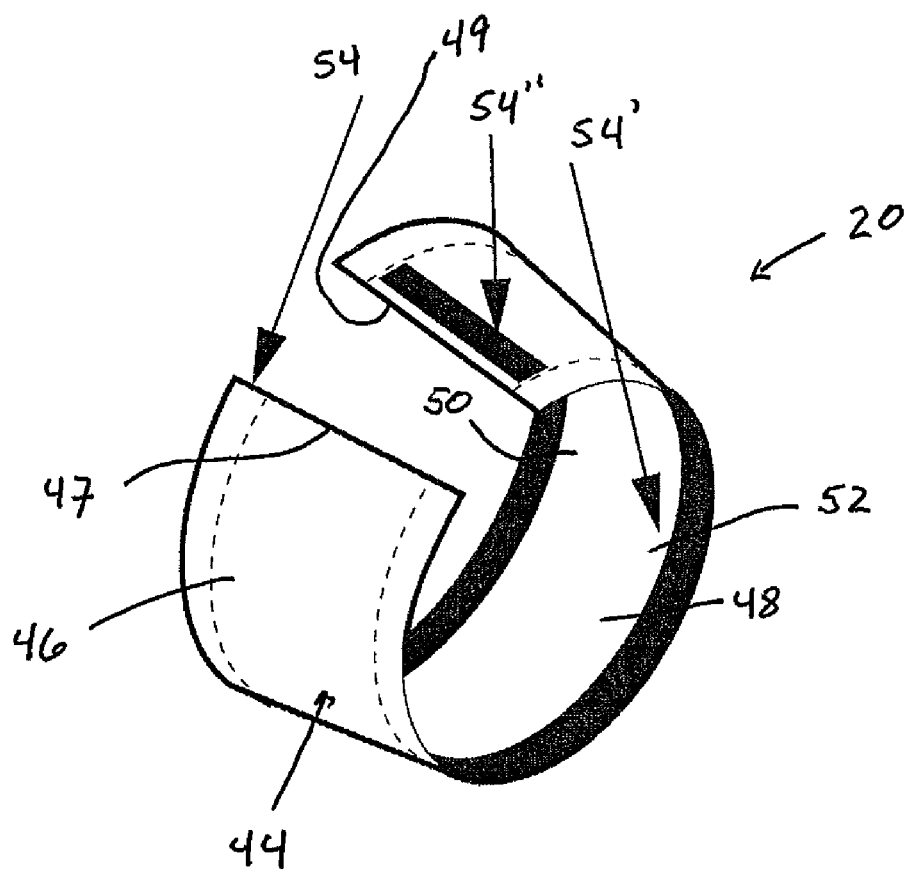
FIG. 7 is a schematic depicting an exemplary cuff of the TOD.

Referring to FIGS. 1 and 7, TOD 10 comprises cuff 20, and a gas impermeable encasement 24 which is divided into an anterior portion 26 and a posterior portion 28. Referring to FIG. 1, anterior portion 26 encloses an anterior side 30 of foot 16 and of lower leg 14, and posterior portion 28 encloses a posterior side 32 of foot 16 and of lower leg 14. Referring to FIG. 2, anterior portion 26 encloses an anterior side 30 of foot 16, lower leg 14, knee 19, and upper leg 23, and posterior portion 28 encloses a posterior side 32 of foot 16, lower leg 14, knee 19, and upper leg 23. Referring to FIGS. 1 and 2 when lateral edges 34 and 36 of anterior portion 26 are merged with lateral edges 38 and 40 of posterior portion 28, TOD 10 forms a chamber 42 which surrounds respective appendages 11 and 11'.

Figure 4:
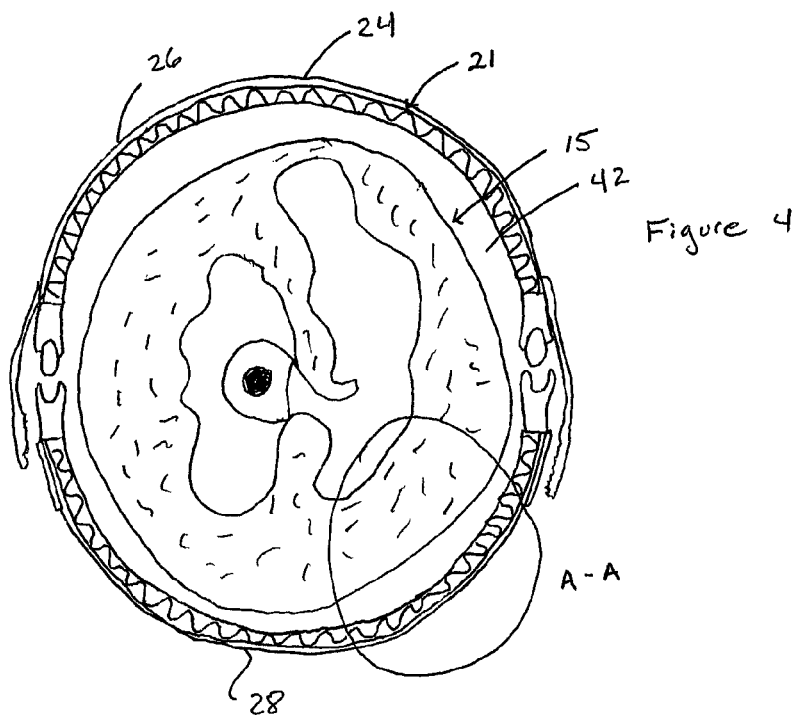
FIG. 4 is a schematic depicting a top view of an exemplary TOD disposed around a target site.
Figure 5:
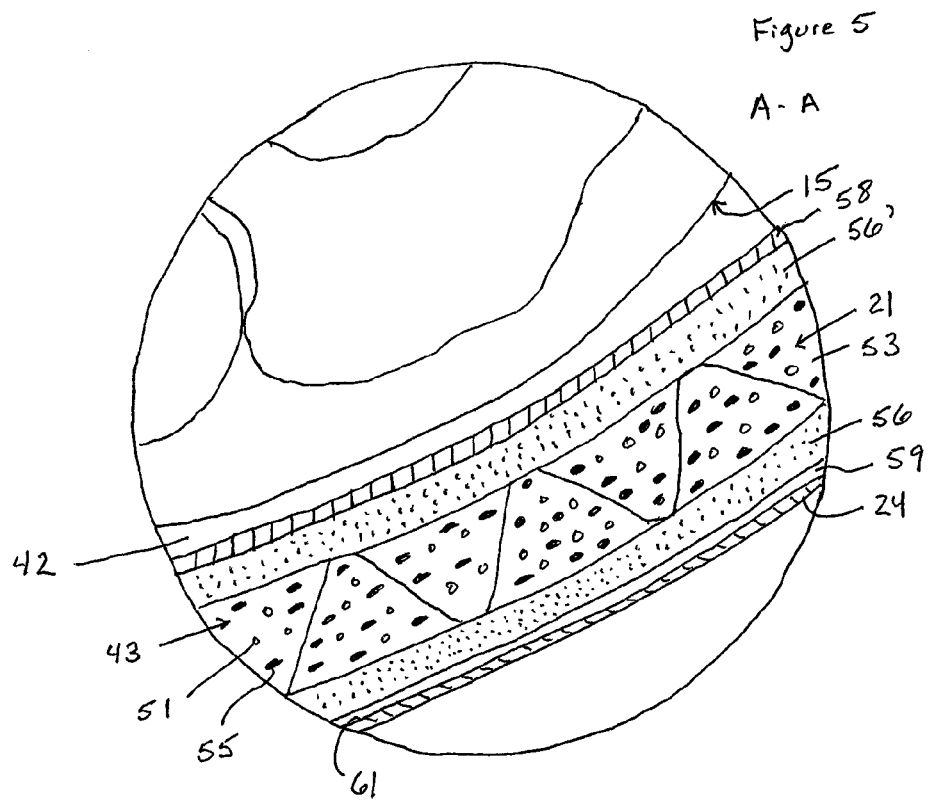
FIG. 5 is a schematic depicting a magnified section A-A of the TOD depicted in FIG. 4.

Referring to FIGS. 4 and 5, TOD 10 further comprises a composite 21, which comprises an oxygen scavenging member 43, a moisture/exudate absorbing layer 56, a moisture/exudate absorbing layer 56', a barrier layer 58, and an adhesive layer 59. Adhesive layer 59 is disposed on an interior side 61 of gas impermeable encasement 24.

Figure 6:
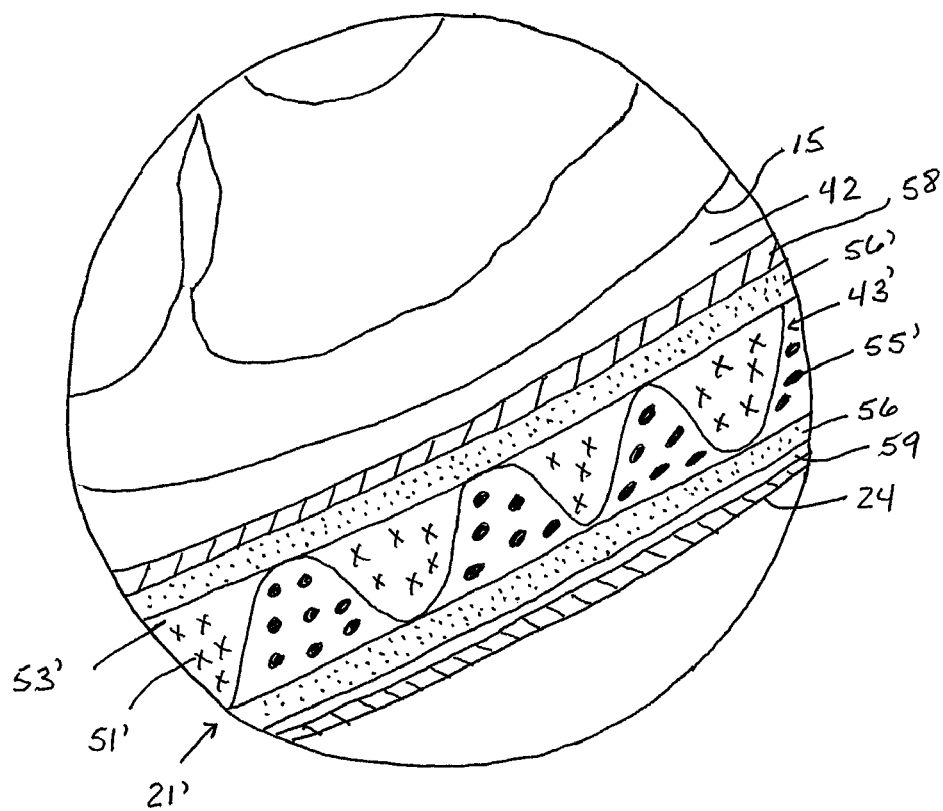
FIG. 6 is a schematic depicting another exemplary composite for use in the TOD depicted in FIG. 4.

Referring to FIG. 5, oxygen scavenging member 43 comprises iron pellets 55 and desiccants 51 randomly distributed into a film 53. Alternatively, referring to FIG. 6, oxygen scavenging member 43' comprises a film 53' comprising alternating groupings of iron pellets 55' and desiccants 51'.

Referring to FIG. 7, cuff 20 comprises a planar body 44 having an exterior side 46 opposite to an interior side 48, and a distal terminal end 47 opposite to a proximal terminal end 49. A proximal surface 50 and a distal surface 52 of interior side 48 each has disposed along a length thereof respective double-sided adhesive strips 54 and 54'. When TOD 10 is in proper use, double adhesive strip 54 attaches to an exterior side 57 at a proximal end 37 of anterior portion 26 of gas impermeable encasement 24, and double adhesive strip 54' attaches TOD 10 to bottom 18 of knee 19.

A double adhesive strip 54" is also disposed on exterior side 46 towards proximal terminal end 49 of cuff 20. Body 44 of cuff 20 may be wrapped over onto itself such that double adhesive strip 54" attaches to interior side 48 of cuff 20 to properly fit TOD 10 to a target site 15. In addition to attaching TOD 10 around a target site, adhesive strips 54, 54', and 54" also assist in creating an air tight seal between TOD 10 and target site 15.

Figure 8:
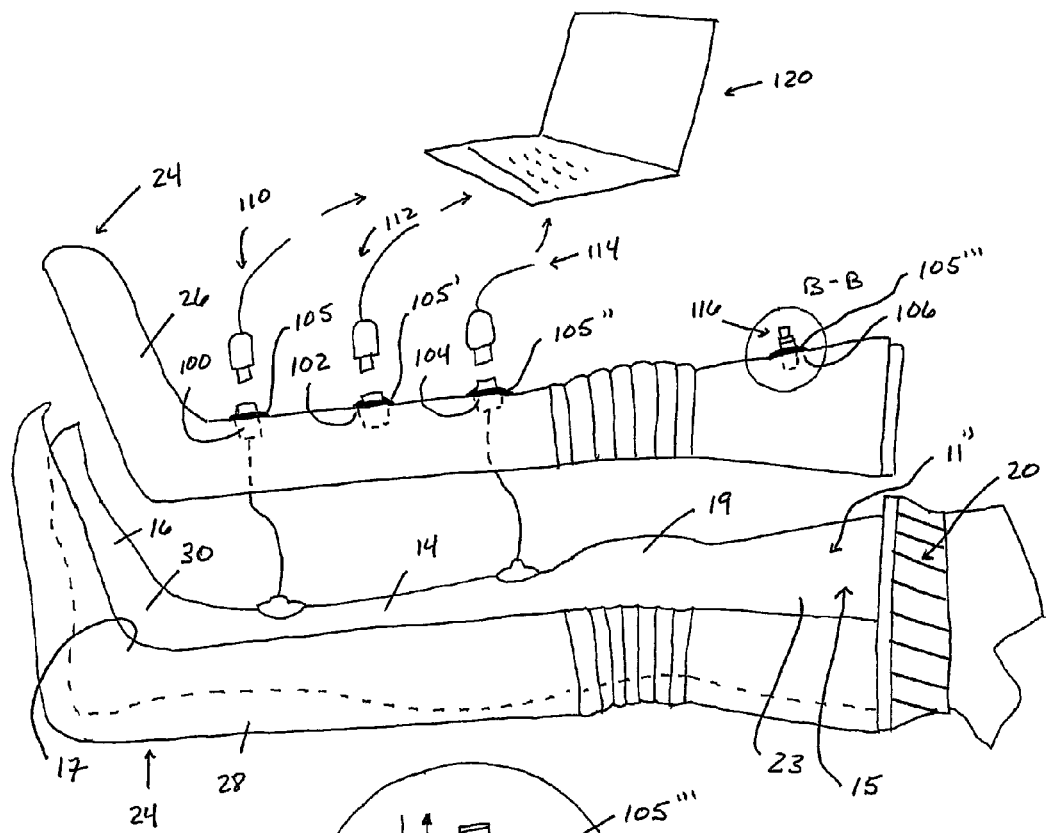
FIG. 8 is a schematic depicting an exemplary use of an exemplary TOD incorporating the gas impermeable encasement depicted in FIG. 2.
Figure 9:
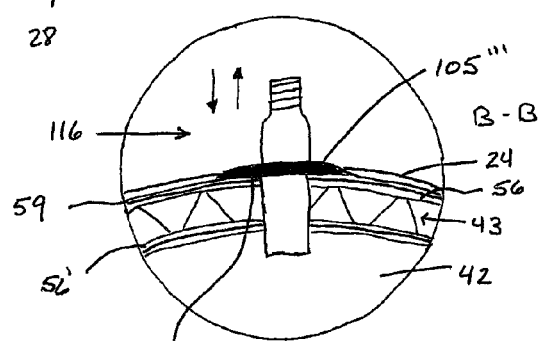
FIG. 9 is a schematic depicting a magnified section B-B.

Referring to FIG. 8, in an exemplary embodiment, anterior portion 26 of gas impermeable encasement 24 has portholes 100, 102, 104, and 106 formed therethrough, wherein each of portholes 100, 102, 104, and 106 comprises a respective rubber seal 105, 105', 105", and 105''' formed around the periphery thereof. A skin oxygenation sensor 110 is disposed on target site 15 and is fitted on and through porthole 100 such that rubber seal 105 is fitted around skin oxygenation sensor 110 so that appreciable amounts of oxygen cannot enter chamber 42 through porthole 100. An oxygen chamber sensor 112 is fitted on and through porthole 102 such that rubber seal 105' is fitted around oxygen chamber sensor 112 so that appreciable amounts of oxygen cannot enter chamber 42 though porthole 102. A skin tissue temperature sensor 114 is disposed on target site 15 and is fitted on and through porthole 104 such that rubber seal 105" is fitted around skin tissue temperature sensor 114 so that appreciable amounts of oxygen cannot enter chamber 42 through porthole 104. A bivalve 116 is fitted on and through porthole 106 such that rubber seal 105''' is fitted around bivalve 116 so that appreciable amounts of oxygen cannot enter chamber 42 through porthole 106. Bivalve 116 controls the flow of gas molecules into and out from chamber 42 and/or from the ambient air. All of skin oxygenation sensor 110, oxygen chamber sensor 112, skin tissue temperature sensor 114, and bivalve 118 are in communication with a computer 120 for purposes of determining, recording, monitoring, and assessing oxygenation of the target site.

Referring to the figures, an exemplary method of using tissue oxygenation device 10 to diffuse oxygen from nearby subcutaneous tissue and capillaries to target site 15 includes applying composite 21 to at least one of anterior portion 26 and posterior portion 28 of gas impermeable encasement 24 by disposing adhesive layer 59 onto interior side 61 such that composite 21 conforms to the shape and contours of interior side 61. Posterior portion 28 may then be positioned over posterior side 32 of appendage 11, and anterior portion 26 may be positioned over anterior side 30 of appendage 11. Anterior portion 26 and posterior portion 28 are then sealed to one another to create an open-end 70 at proximal end 37 of encasement 24 and a closed end 39 at a distal end 33 of encasement 24.

Cuff 20 is applied to proximal end 37 to close off open-end 70 and to seal target site 15 within chamber 42. In an exemplary embodiment, adhesive 54 is disposed on exterior side 57 at proximal end 37 of gas impermeable encasement 24, adhesive 54' is applied to bottom 18 of knee 19, and adhesive 54" is disposed on an interior side of body 44 of cuff 20 so that cuff 20 seals target site 15 within chamber 42.

Referring to FIG. 8, in an exemplary embodiment, the method may further comprise purging chamber 42 of oxygen, wherein purging occurs at the point of initiating the non-hyperbaric treatment process to shorten the time needed to obtain the lower oxygen concentration in the chamber which is necessary for establishing the oxygen gradient and diffusion to occur. In an exemplary embodiment, a nitrogen gas is delivered into chamber 42 through bivalve 116, while the oxygen initially contained in chamber 42 is extracted through bivalve 116.

Once tissue oxygenation device 10 is applied to the target site as set forth and described above herein, the oxygen scavenger contained in oxygen scavenging member 43 and 43', continuously and steadily removes oxygen contained within chamber 42. As this causes the oxygen concentration within chamber 42 to be lower than the oxygen concentration in the nearby subcutaneous tissue and capillaries, oxygen from the nearby subcutaneous tissue and capillaries flows through and over target site 15 and into chamber 42. As the oxygen scavenger is continuously removing oxygen from chamber 42, the diffusion of oxygen from the subcutaneous tissue and the capillaries and out into chamber 42 occurs continuously. Accordingly, the increase in oxygenation through and over the target site is obtained by the continuous flow of oxygen molecules moving along the concentration gradient formed by the continuous removal of oxygen from chamber 42 by the oxygen scavenger.

It should be understood that other, obvious structural modifications can be made without departing from the spirit or scope of the invention. Accordingly, reference should be made to the accompanying Claims, rather then the foregoing description, to determine the scope of the invention.

What is claimed is:

1. A tissue oxygenation device for promoting the diffusion of oxygen from underlying capillaries and subcutaneous tissue up through and over an overlying target site of skin tissue, comprising:
    a gas impermeable encasement which forms a chamber which surrounds the target site when the encasement is positioned over the target site;
    an oxygen scavenging member comprising:
        a thermoplastic film; and
        an oxygen scavenger comprising an oxygen absorbent which is dispersed in the thermoplastic film;
        wherein the oxygen scavenging member is contained within the chamber such that the oxygen scavenger is exposed to oxygen within the chamber, and further wherein the oxygen scavenger removes oxygen contained within the chamber at a continuous rate;
    an adjustable cuff, wherein the adjustable cuff comprises a pliable body which is attached to the gas impermeable encasement on an end of the body and to the target site at another end of the body, wherein the gas impermeable encasement and the adjustable cuff jointly operate to seal the target site within the chamber; and
    one or more portholes formed through the gas impermeable encasement, wherein the one or more portholes is surrounded at an outer periphery thereof by a rubber seal,
wherein the one or more portholes receives at least one of a chamber oxygen sensor, a skin tissue oxygenation sensor, and a skin tissue temperature sensor.

2. A tissue oxygenation device for promoting the diffusion of oxygen from underlying capillaries and subcutaneous tissue up through and over an overlying target site of skin tissue, comprising:
    a gas impermeable encasement which forms a chamber which surrounds the target site when the encasement is positioned over the target site, wherein the gas impermeable encasement comprises an anterior portion and a posterior portion, wherein the anterior portion is fitted around an anterior side of the target site, and the posterior portion is fitted around a posterior side of the target site, and wherein each of the anterior portion and the posterior portion comprises a first lateral edge opposite to a second lateral edge, wherein the first lateral edges of the anterior and posterior portions are joined to each other to form a seal therebetween, and wherein the second lateral edges of the anterior and posterior portions are joined to each other to form a seal therebetween;
    an oxygen scavenging member comprising an oxygen scavenger, wherein the oxygen scavenging member is contained within the chamber such that the oxygen scavenger is exposed to oxygen within the chamber, and further wherein the oxygen scavenger removes oxygen contained within the chamber at a continuous rate; and
    an adjustable cuff, wherein the adjustable cuff comprises a pliable body which is attached to the gas impermeable encasement on an end of the body and to the target site at another end of the body;
wherein the gas impermeable encasement and the adjustable cuff jointly operate to seal the target site within the chamber.

3. The tissue oxygenation device of claim 2, wherein the anterior portion is sealed to the posterior portion to create a gas impermeable encasement having a closed distal end opposite to an open-ended proximal end.

4. The tissue oxygenation device of claim 3, wherein the pliable cuff is attached to the open-ended proximal end to close off the open-ended proximal end such that the target site is sealed within the chamber.

5. The tissue oxygenation device of claim 4, wherein the pliable cuff comprises a body having an exterior side opposite to an interior side, and wherein the tissue oxygenation device further comprises a first adhesive and a second adhesive both attached to the interior side of the cuff, and a third adhesive attached to the exterior side of the cuff, wherein:
    the first adhesive is disposed on the posterior portion and on the anterior portion of the gas impermeable encasement;
    the second adhesive is disposed on the target site; and
    the third adhesive is disposed on the interior side of the cuff to fix a diameter of the cuff;
wherein the disposal of the first adhesive, the second adhesive, and the third adhesive onto their respective sites creates a seal between the chamber and the target site.

6. The tissue oxygenation device of claim 5, wherein the target site comprises skin tissue located on an appendage comprising an upper leg, a knee, a lower leg, an ankle, and a foot, and wherein:
    the closed distal end of the gas impermeable encasement surrounds the foot, and the open-ended proximal end of the gas impermeable encasement surrounds the upper leg; and the cuff is disposed around the upper leg and closes off the open-ended proximal end to seal the upper leg within the chamber.

7. The tissue oxygenation device of claim 5, wherein the target site comprises skin tissue located on an appendage comprising a foot, an ankle, a lower shin, and a lower calf wherein:
the closed distal end of the gas impermeable encasement surrounds the foot, and the open-ended proximal end of the gas impermeable encasement surrounds the lower calf and the lower shin; and the cuff is disposed around the lower calf and the lower shin and closes off the open-ended proximal end to seal the lower calf and the lower shin within the chamber.

* * * * *